United States Patent [19]

Hogg et al.

[11] 4,286,876
[45] Sep. 1, 1981

[54] APPARATUS AND METHOD FOR MEASURING SCATTERING OF LIGHT IN PARTICLE DETECTION SYSTEMS

[75] Inventors: Walter R. Hogg, South Miami; Albert Brunsting, Miramar, both of Fla.

[73] Assignee: Coulter Electronics, Inc., Hialeah, Fla.

[21] Appl. No.: 438

[22] Filed: Jan. 2, 1979

[51] Int. Cl.³ .......................................... G01N 21/00
[52] U.S. Cl. ................................... 356/343; 250/574; 350/103; 350/292
[58] Field of Search ...................... 356/336, 338, 343; 250/574; 350/103, 109, 167, 211, 292, 320

[56] References Cited

U.S. PATENT DOCUMENTS 3,508,830   4/1970   Hopkins et al. ...................... 356/338

FOREIGN PATENT DOCUMENTS 170219   1/1960   Sweden ................................... 250/574

Primary Examiner—John K. Corbin
Assistant Examiner—Matthew W. Koren
Attorney, Agent, or Firm—Silverman, Cass & Singer, Ltd.

[57] ABSTRACT

In an apparatus in which particles are passed through an optical sensing zone to measure their light scattering characteristics for the purpose of identifying the particles, means and a method are provided for deviating the collected light in accordance with predetermined different paths to a plurality of different photodetecting devices. The deviation is effected simultaneously with collection by optical radiant energy reflecting means. The different photodetecting devices enable the measurement of energy scattered along the particular path which is identified with that device. The paths are established by the combined collecting and deviating means rather than permitted to evolve by the scattering phenomena themselves whereby the photodetecting devices can be located in convenient arrangements and may be conventional in construction.

30 Claims, 6 Drawing Figures

APPARATUS AND METHOD FOR MEASURING SCATTERING OF LIGHT IN PARTICLE DETECTION SYSTEMS

BACKGROUND OF THE INVENTION

This invention is concerned generally with the measurement of scattered light and more particularly is concerned with the measurement of the energy and direction of light scattered by particles passing through an optical sensing zone whereby to enable the identification of the particles and/or their characteristics.

The invention herein has relatively wide application but particularly is of value in the identification of white blood cells, cancer cells and other biological particles.

There is a considerable body of literature and prior art on the work which has been done by others in the identification of biological cells and it would be of some value to review the same briefly. It would be advantageous also to delineate the relationship of this invention with the apparatus which has been utilized and is described in the prior art.

Basically, a sensing zone is established in some way by directing a beam of concentrated light to a small volume through which the particles are to be passed, the particles are directed to pass through the zone and the scattered light is detected in different geometric locations around the zone. Scattering may occur backward or forward of the zone relative to the light source. The zone is usually called a scattering point.

In its simplest form, a stream of liquid or air carrying the particles is flowed through a pipe and at a transparent location along the pipe a beam of light is projected across the stream. A photodetector on the side of the pipe opposite the source of the beam of light will detect a change in its response each time that a particle passes. Obviously the fact of change enables the particles to be counted. The "shadow" thrown by the particle on the photodetecting device provides some information as to size. Other photodetecting devices can be positioned at locations spaced from the axis of the light beam to give signals which are related to the amount of light scatter in different polar locations. The direct beam can be blocked out and only the scattered light measured, if desired.

In biological cells, the condition of the interior of the cell will produce scattering of light in different ways and many of the apparatuses of the prior art are concerned with the method and techniques whereby the effects of light scattering help identify the cells.

Identification of the cells, especially white blood cells, is needed for diagnosis and detection of disease, for the ascertaining of patient condition and the effects of therapy, etc. Present methods and apparatus for this purpose are channeled toward the automation of the identification techniques to enable high speed measurements and positive identification. This is to enable the elimination of the slow, tedious and inaccurate manual methods that have been classically practiced in laboratories, clinics and hospitals.

The systems and apparatus which are known utilize a fluid flow which tends to pass the particles to be measured through a sensing zone one by one. Although the fluid may be a gas, generally in the study of biological particles this is a liquid such as a saline solution whose purpose importantly is to preserve the integrity and the condition of the particles. Gas and air as fluids for transporting particles to and through sensing zones are used more commonly in the study of industrial particles such as fly ash, dust, comminuted minerals etc.

Considering principally biological particles (although the prior art to be mentioned is not necessarily limited thereto) typically such particles are entrained in a sheath of liquid which is either circular or almost flat planar in cross section at the sensing zone. Several U.S. patents which disclose this type of entrainment and sensing zone are: Nos. Re. 29,141; 3,413,464; 3,657,537; 3,705,771; 3,785,735 and 3,791,196.

After the particle passes into the sensing zone, the light or other radiant energy which has been directed at the sensing zone by some means such as a concentrated lamp beam or a laser is measured at different locations relative to the sensing zone. Typical of these devices are several of those mentioned above as well as in U.S. Pat. No. 3,835,315. A system for such measurements is disclosed in U.S. Pat. No. 4,070,113 although the photodetector therein is not described in much detail.

The problem of measuring the scattered light at different locations has been attacked by others but three important disadvantages have been difficult to overcome. The first is the disadvantage of not being able to get enough information because of the difficulty of measuring a plurality of points. The second is the disadvantage of complex and difficult to manufacture apparatus with its attendant companion disadvantage of great expense. The third is the disadvantage of not getting enough energy from the scattered light at all measuring points to give meaningful data.

Each of the four prior art references mentioned hereinafter has one or more of these disadvantages.

The oldest of these references is U.K. Pat. No. 137,637 of 1920 to Pollard which utilizes expensive conical frustums and reflecting prisms. The scattered light is viewed by a microscope and/or measured by crude means compared to those available at the present time.

The second of these references is Frommer U.S. Pat. No. 3,248,551 which utilizes a compound type of annular reflector that has two surfaces and concentrates the scattered light captured by the respective surfaces and reflects same to separate photomultiplier tubes. It is quite obvious from an examination of this patent that the twosurface reflecting device is most difficult and complicated to manufacture; hence one which would require collection from many more than just two angles or polar regions would be even more difficult and expensive to manufacture. In this structure, the collection and deviation of the scattered radiant energy is effected by a single element.

Neither the Pollard nor the Frommer patent has the simplicity and efficiency of the present invention. The number of regions of light scatter from which information can be obtained is severely limited in these prior art devices.

The third and fourth of these references comprise two publications describing a device which is mentioned in U.S. Pat. No. 4,070,113 as a type of photovoltaic detector which has concentric rings formed on a disc that is several inches in diameter. The light from the scattering zone is permitted to fall directly onto this detector which then provides electrical signals related to the energy of the light at different distances from the center of the beam. The publications are an article entitled "Light-Scattering Patterns of Isolated Oligodendroglia" By R. A. Meyer, et al in *The Journal of Histo-*

*chemistry and Cytochemistry,* Vol. 22, No. 7, pp 594-597, 1974 and a second article entitled "Gynecologic Specimen Analysis by Multiangle Light Scattering in a Flow System" by G. C. Salzman et al in the same Journal, Vol. 24, No. 1, pp 308-314, 1976. In the articles reference is made to the same or a similar detector device which is identified as a Recognition Systems, Inc. detector.

The ring detector which has been described above is quite expensive at the present time. It typically comprises 64 photodiodes arranged in rings and wedges, all on the same substrate. If any element or increment of the detector fails or is damaged the entire device may have to be discarded. Additionally, the contacts for the diodes are brought out to a narrow edge segment at which point they are required to be connected into electrical circuitry. This is a delicate and precise operation not easily effected by unskilled technicians.

Additionally, the inner rings are very small while the outer rings are quite large. Thus the radiant energy is weakly diffused over the outer rings giving low power density. Additionally the electrical capacitance of the outer rings is substantially high which results in loading and deterioration of signal. This is a problem where the particles which move through the sensing zone at high speed generate light pulses which may be as short as a microsecond.

The basic difference between the invention and the methods and apparatus which are known lies in the manner in which control of the scattered light is achieved.

The invention herein solves the problems of the prior art to eliminate the disadvantages thereof through the use of a composite spherical mirror which receives the scattered radiant energy from a sensing zone and deviates specific geometric areas thereof to different locations, the locations being spaced from one another and the deviation being in a direction folded back towards the sensing zone. The fact that there are different locations where the radiant energy is caused to confluence enables the use of totally independent photoconductive devices at the respective locations for measurement of the specific portions of radiant energy from the different geometric areas.

The independent photoconductive devices are located in any convenient array, are conventional in construction and hence are highly economical and easily replaced independently. The capacitance to ground is low permitting rapid voltage change and good response thereby preserving the amplitude of electrical signals resulting from the high speed passage of particles. The light is concentrated on a small photosensitive area resulting in the highest power density possible with consequently high signal-to-noise ratio.

The invention permits of considerable latitude in configuration, placement, construction and arrangement thereby providing high flexibility for almost any kind of system, but also with no loss in convenience and economy of use.

SUMMARY OF THE INVENTION

Method and apparatus for measuring the scattering of light in particle detection systems.

Particles are directed through a sensing zone which preferably has them passing in such a manner that they traverse it essentially one-by-one. The zone is established by directing a beam of radiant energy such as visible light to the zone and detecting the passage of the particle through the zone by response of a photodetecting device to the disturbance of the quiescent beam. Reflective means are used to collect and simultaneously to cause deviation of the radiant energy caused by characteristic scatter from its normal pattern to those which are predetermined by suitable design of the reflective means whereby to direct the scatter beams to particular photodetecting devices or photoresponsive areas arranged in a convenient array. Conventional photodetecting devices may be used for this purpose.

The collecting and deviating means comprise a composite spherical mirror made up of annular rings of different size, each tilted relative to the central optical axis of the mirror to direct the reflected beams of the respective ring to confluence at different locations where the radiant energy confluenced at the said locations can be measured independently.

DESCRIPTION OF THE PREFERRED EMBODIMENTS

According to the invention, the method comprises providing a sensing zone or scattering point and passing particles through this sensing zone to sense their presence and to direct radiant energy thereon for that purpose. Each particle scatters the radiant energy and this scattered radiant energy is collected and deviated by suitable optical means and focussed or confluenced towards a point in space, but the deviation is effected by an assembly of elements which causes the energy in the different angles or paths or geometric parts to be deviated to different locations for the convenience of measuring them. The measurement is effected by an array of photodetecting devices or elements which respond respectively to the intensity of energy present in the particular angle, path or part. From this data, by reason of information which is known from previous studies, one can identify and/or determine the character of the particle which produced the scattering.

The invention is believed to provide more scattering data and of higher definition than known methods and apparatus which use reflection only as a result of which it is useful for the establishment of information related to specific types of particles by passing known particles into the sensing zone in order to learn the scattering effects of such particles for use in other work where unknown particles are being identified.

In a specific sense, the scattered energy can be thought of as hollow or solid cones of light or radiant energy each of which is brought to a focus or point of confluence at the location of the photoresponsive device or element which is intended to make the measurement for that specific cone. The scattered energy can also be measured as part cones for additional information, as for example when the energy may not be in symmetrical geometric form, although this is unusual.

The novelty of the invention lies principally in forming a spherical mirror out of a plurality of annular optical elements or segments which "point" or are focussed in specific different directions to enable the energy deviated thereby to be confluenced and measured. The elements may be assembled in a single integrated member whereby the practical thickness of the resulting element is much less than it would be if complete individual elements were used.

Figure 1:
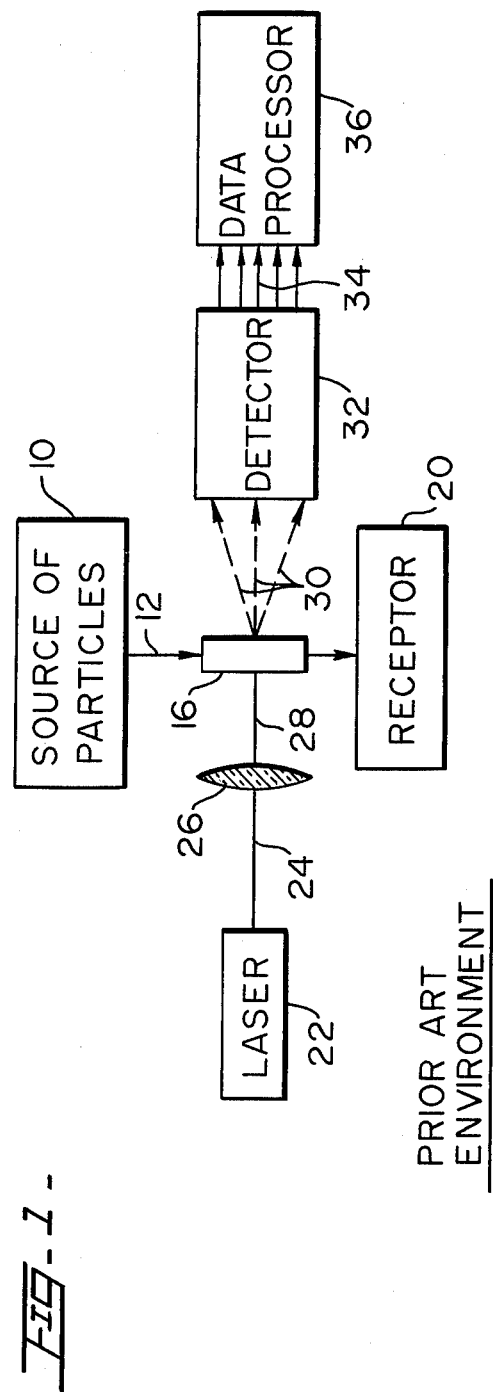
FIG. 1 is a diagrammatic view of the prior art environment in which the invention is utilized.

FIG. 1 illustrates a prior art system which shows the environment in which the invention is utilized. Here a source of particles 10 is provided which may feed, for example, white blood cells, exfoliated cells or the like in a diluent by way of the path 12 to the flow-through element 16. This may be effected in this simple flow or with some additional second diluent which produces a particular form of geometric cross section of fluid in a sensing zone. The additional diluent may comprise a stream of liquid under pressure surrounding the main flow to produce sheath flow conditions through the body of the liquid whereby to confine the particle stream. The basic stream itself may form a flat planar stream through the sensing zone.

From the flow-through element 16, the fluid that has been passed through moves along the path 18 to a suitable receptor 20 which may be waste, another system or an accumulator.

The source of radiant energy is here shown as a laser 22 but can be any suitable source of light or the like. The invention provides an efficiency which enables the laser used to be of low power with a minimum of heat generation. The resulting beam is passed along the optical axis 24 to an optical system or train represented by the lens 26 which focusses the radiant energy onto the sensing zone of the flow-through element 16, the emergent light being scattered and providing a plurality of radiating beams indicated at 30. Only three such beams are shown as representative, there being an infinite spread of the energy, the amount of radiant energy at any diverging angle and in any sector being dependent upon the size, character and composition of the particle which produced the scattering. A detector 32 is provided which is ideally constructed to respond differently at its different geometric aspects facing the beams 30 so that at incremental locations over the area of its frontal aspect it will produce different identifiable signals, notably, signals of different intensities. These signals are passed through the channels 34 to some form of data processor 36. From the signals and their relationship to one another, both as to intensity and geometric location, the particle which produced the signals may be identified or at least characterized.

The detector 32 of the prior art of necessity had a limited number of photoresponsive elements in its array because the pattern of scattering was not controlled. The scattered light is diffused; the part of the total solid angle of available radiant energy represented by rays 30 is small. Special detectors such as mentioned hereinabove were complex and expensive. In the invention, since the pattern of the scattered radiation is altered to almost any which is desired and the areas of such radiation may be welldefined, the limitations on number and size of the array of photodetectors are less stringent.

One could say that the combined radiant energy deviating means and array of photodetectors of the invention is the element identified as 32 in FIG. 1.

Figure 2:
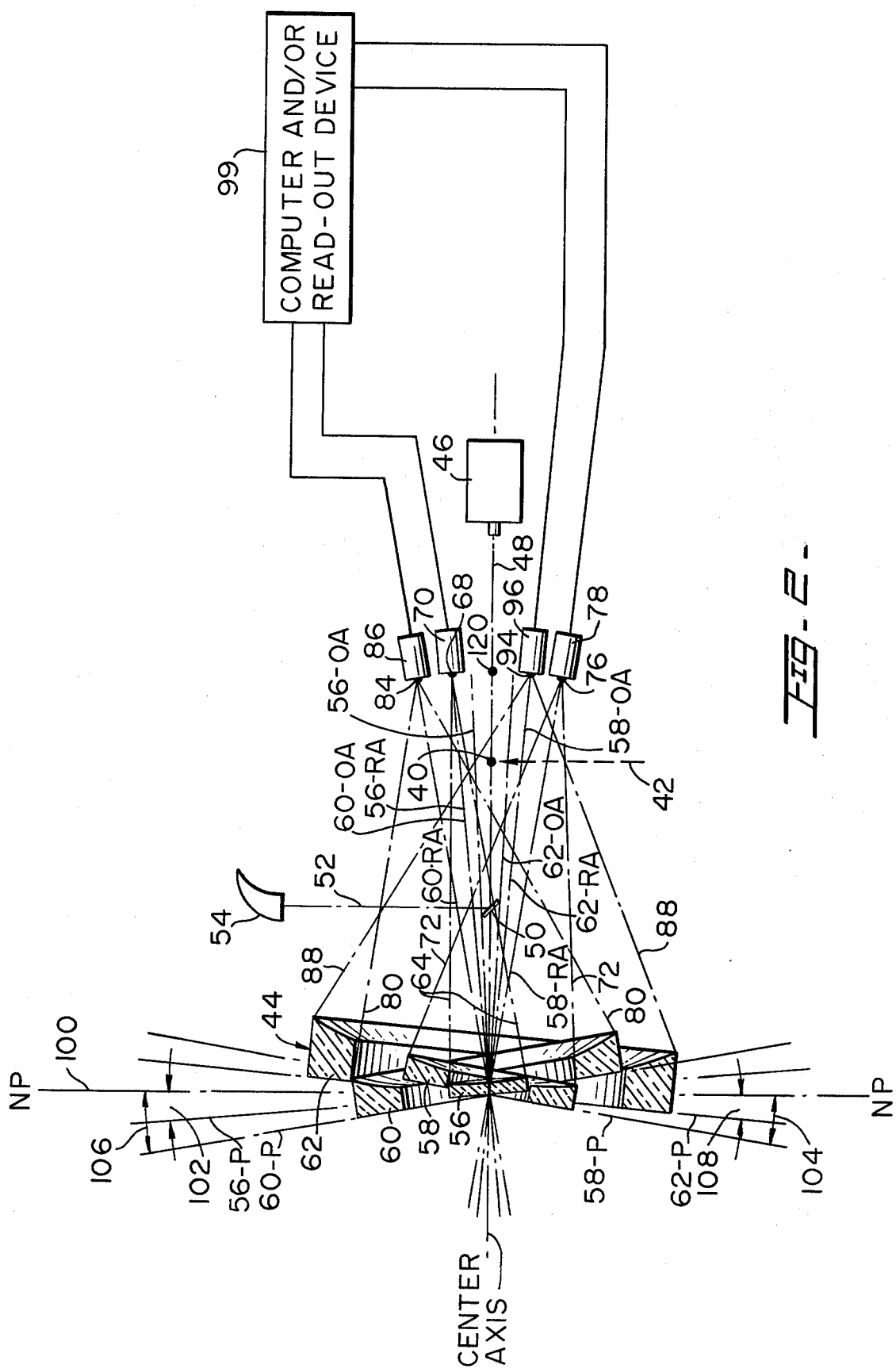
FIG. 2 is a diagrammatic generally sectional view through a simplified form of the composite mirror of the invention showing the manner in which the scattered light from the sensing zone is collected and deviated to the photoresponsive devices.

A preferred embodiment is illustrated in FIG. 2 which shows what may be termed the scattering point or sensing zone 40 through which particles may be moved from a lateral source (not shown) along the path 42. These particles would be entering the sensing zone 40 preferably one at a time and, as mentioned, for biological particles may be entrained in a liquid confined by sheath flow. Although not here illustrated, the entire structure including the sensing zone 40 and the shortly-to-be-described collecting and deviating device 44 may comprise a container for a body of liquid whose refractive index is identical to that of the liquid entraining the particles.

The source of radiant energy in the apparatus illustrated is a laser 46 whose fine beam is directed along a principal optical axis 48 intersecting the path 42 at the scattering point 40. This axis will be used as a reference axis for the explanation and the parts of the device 44 are tilted relative thereto; hence the axis is designated "CENTER AXIS" in FIG. 2. It is an extension of the optical axis 48. Radiant energy not scattered but passing the point 40 is captured by a small angled mirror 50 and directed laterally along the path 52 to a light dump 54. The portion of the radiant energy which is scattered in all directions which is collected is that which is scattered forward (to the left of the scattering point in FIG. 2) by a composite mirror 44 and deviated by being reflected back toward the scattering point 40, but on axes which are substantially deviated from the axis 48.

The radiant energy which is collected by the composite mirror 44 is selectively collected by the concentric rings 56, 58, 60 and 62 which comprise the mirror 44 and is caused to confluence at locations lateral of the axis 48. Individual photodetectors located at the respective locations of confluence can measure the intensity of radiant energy at these points, and, since each photodetector is individual to a particular one of the rings, it furnishes information only related to that ring.

For simplicity, it is assumed that the mirror 44 is formed out of four individual annular rings 56, 58, 60 and 62 which are tilted relative to the axis 48 vertically only. Each annular ring collects only a ring of scattered energy impinging on its mirrored surface and deviates that geometric portion by twice the angle between its tilted optical axis and the center axis 48 to a lateral point of confluence (up or down in this arrangement).

Figure 3:
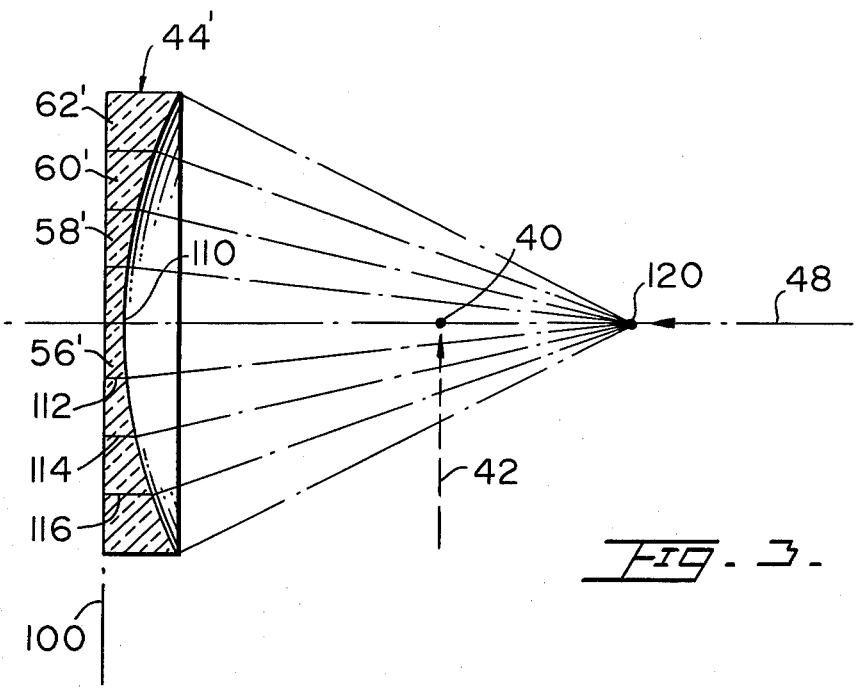
FIG. 3 is a diagrammatic view similar to that of FIG. 2 but showing the spherical mirror from which that form of FIG. 2 is derived.

For this illustration and ease of understanding, it has been assumed that the rings of the composite mirror 44 have been cut or otherwise formed from a complete mirror and that if put back together, the rings would produce a complete mirror as indicated in FIG. 3 at 44', all rings having their rear surfaces lying in a common plane. Thus, each of the rings 56, 58, 60 and 62 has the plane of its rear surface identified in FIG. 2 by a reference character with the suffix P. The view being a section, each plane is shown by a broken line. Prior to separation, the rings of the spherical mirror would have the appearance as at 56', 58', 60' and 62' but when separated and tilted they are as in FIG. 2. (As mentioned hereinafter, they may also be rotated).

Each of the rings is tilted by a different angle, in the particular simplified form there being two rings tilted upward relative to the scattering point and two tilted downward. As indicated, the tilting is vertically for simplified explanation.

The center ring 56 is the smallest of the rings which are derived from the spherical mirror 44' and it has been tilted upward slightly relative to the center axis 48 and the scattering point 40. The plane of the rear surface of the ring 56 is identified at 56-P, and the plane 100 which is normal to the center axis 48 is identified at NP. This would coincide with the plane of the rear surface of the mirror 44' in FIG. 3. The angle between the normal plane 100 and the rear plane 56-P of the ring 56 is shown at 102. The same angle obtains between the central axis 48 and the optical axis of the ring 56, the latter being identified as 56-OA. The focus or point of confluence of the ring 56 will, however, be along an axis which makes an angle relative to the central axis 48 that is twice the angle of tilt 102, it being a reflective axis. This is identified as the axis 56-RA and the focal point is at 68. The distance from the ring 56 to the focal point or point of confluence 68 depends upon the curvature of the reflective surface of the ring. For the purpose of this simplified version of the invention, it is taken that all rings are derived from the same spherical mirror; hence all of the points of confluence or focal points will be at substantially the same distance from the mirror 44.

A first photodetector 70 is located to respond to the confluenced energy from the ring 56. The ring 56 has collected a cone of radiant energy from that scattered forward from the scatter point 40 and has deviated same in a solid angle cone whose outer extent is defined by the surface 64. Since the angle of ring 56 is solid, the cone of radiant energy is also solid.

The next outer ring 58 is annular, has been slightly tilted downward relative to the scatter point 40 so that its rear plane 58-P makes an angle 104 with the normal plane 100, its optical axis 58-OA making the same angle with respect to the central axis 48. The reflective axis 58-RA of the ring 58 is at an angle with the central axis 48 that is twice the angle 104 and the focal point or point of confluence 76 occurs on that axis. The cone of radiant energy which is collected and deviated by the ring 58 is hollow, being defined by an inner conical surface (not shown) and the outer conical surface 72. The confluenced radiant energy from the ring 58 is focussed on the face of the second photodetector 78.

The next outer ring 60 is also annular, has been tilted upward relative to the scatter point 40 so that its rear plane 60-P makes an angle of tilt 106 with the normal plane 100, its optical axis 60-OA making the same angle with respect to the central axis 48. The reflective axis 60-RA of the ring 60 is at an angle with the central axis 48 that is twice the angle 106 and the focal point or point of confluence 84 occurs on that axis. The cone of radiant energy which is collected and deviated by the ring 60 is hollow, being defined by an inner conical surface (not shown) and the outer conical surface 80. The confluenced radiant energy from the ring 60 is focussed on the face of the third photodetector 86. It will be noted that in the view, the reflective axis 56-RA and the optical axis 60-OA happen to coincide because of the particular choice of angles. It should be understood that there are two lines representing axes one on top of another.

The outermost ring 62 is also annular, has been tilted slightly downward relative to the scatter point 40 so that its rear plane 62-P makes an angle of tilt 108 with the normal plane 100, its optical axis 62-OA making the same angle with respect to the central axis 48. The reflective axis 62-RA of the ring 62 is at an angle with the central axis 48 that is twice the angle 108 and the focal point or point of confluence 94 occurs on that axis. The cone of radiant energy which is collected and deviated is hollow, being defined by an inner conical surface 90 (FIG. 4) and an outer conical surface 88. The confluenced radiant energy from the ring 62 is focussed on the face of the fourth photodetector 96. It will be noted that in the view, the reflective axis 62-RA and the optical axis 58-OA happen to coincide because of the particular choice of angles. It should be understood that there are two lines representing axes one on top of another.

All of the photodetectors 70, 78, 86 and 96 are coupled to a computer and/or readout device 99 which provides identification of the particles through comparison of the received data with previously stored or recorded data.

The mirror 44 has been described thus far as made up of four rings which have been described individually. Also the spherical mirror 44' from which this mirror 44 has been derived is described in connection with FIG. 3. Inviting attention to FIG. 3 there is illustrated a scattering point 40, a particle stream 42 and the laser beam path 48 which coincides with the center optical axis of the mirror 44', being directed at the optical center of the spherical mirror 44'. The front surface 110 of the spherical mirror 44' which faces the scattering point 40 is presumed to be reflective. The rear base plane 100 is the same as in FIG. 2 except that in this case there is actually an integral surface defining this rear or normal plane as it is referred to in connection with FIG. 2.

The mirror 44' is shown divided into four annular rings 56', 58', 60' and 63' by the cylindrical dividing interfaces 112, 114 and 116 that are coaxial with the axis 48.

Until and unless the mirror 44' is separated into the annular rings 56', 58', 60' and 62' and these rings are reoriented relative to the axis 48, all radiant energy collected by the surface 110 will focus at a point 120 on the axis 48. The points 40 and 120 may be coincident or spaced from one another, but the further the point 120 is from the mirror 44', the less degree of tilt is required of the rings to achieve any desired lateral spacing of the points 68, 76, 84 and 94 (FIG. 2). If the mirror 44' is cut into the four rings described along the interfaces 112, 114 and 116 and the individual rings tilted as described in FIG. 2, the mirror 44 will result. For purposes of illustration, the focal point 120 is also indicated in FIG. 2, but it is understood that none of the rings will be tilted to focus at this point since the laser beam would thereby be blocked.

In practical versions of the invention, a master can be made by actually forming the mirror 44', cutting it into individual rings, tilting the rings, fixing them in their tilted positions by suitable cement and shaving the rear surface to a plane generally parallel with the normal plane 100 in order to render the composite assembly as thin as possible and with a flat rear surface. This master can then be used to mold many composite lenses similar to 44 out of suitable plastic or other material which is amenable to having its front surface silvered.

There may be many more rings than four and the orientation may include rotation to achieve circumferential spacing around the axis 48 relative to one another to establish and space the points of confluence and hence the locations of the photodetectors in any desired configuration. The configuration may be in a vertical or horizontal line, in arcs, in a circle around the axis, etc.

This provides almost universal flexibility in the placement of the photodetectors which can be conventional in their construction and hence quite economical and individually replaceable.

Figure 4:
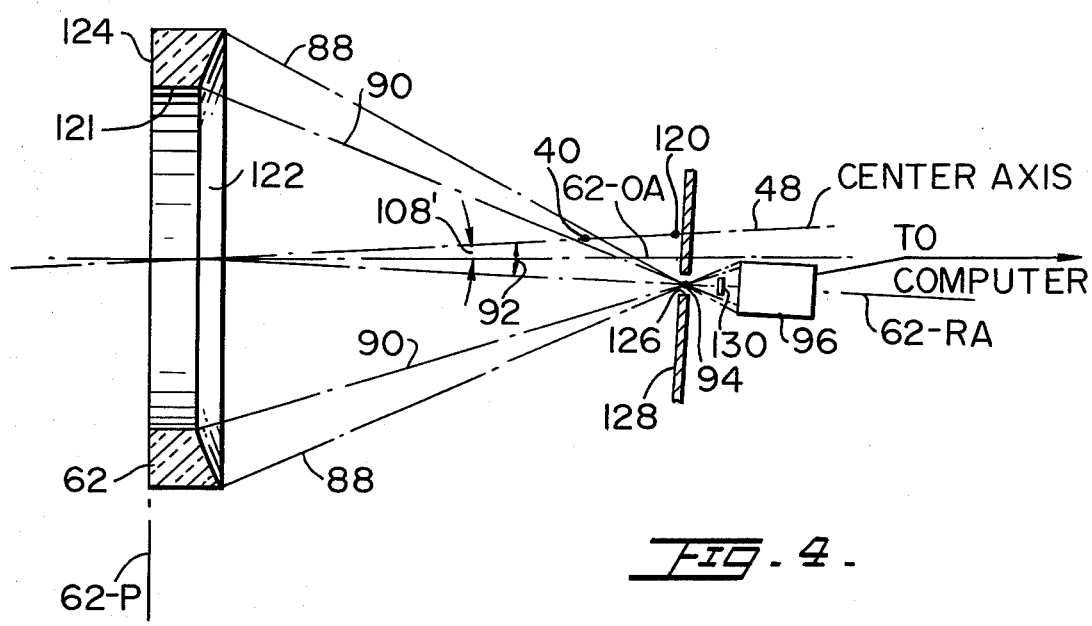
FIGS. 4 and 5 are diagrammatic fragmentary generally sectional views of structures used in apparatus such as shown in FIG. 2 to enhance the operation thereof by purifying the beams of radiant energy reaching the respective photodetectors.

FIG. 4 shows a part of the system of FIG. 2 in which purification of the radiant energy collected and deviated by one ring is effected. The only ring shown is the outermost one, namely, 62, and in the view one can see the central inner surface 120, the reflective front surface 122, the rear surface 124, the optical axis 62-OA of the ring 62 and its reflective axis 62-RA. The center axis 48 is shown, this being the axis of reference. In this view, the manner in which the radiant energy is deviated is clearly illustrated. The tilt downward of the ring 62 is here shown at 108', this angle being identical to the angle 108 of FIG. 2. Note that this angle 108' is measured between the center axis 48 and the optical axis 62-OA of the ring 62. Since the radiant energy enters the mirror surface 122 already at an angle, there will be an angle of reflection equal to the angle of incidence, and hence the total angle of deviation relative to the axis 48 is twice the angle 108' and is designated in the view as 92. The hollow cone of deviated radiant energy which is defined by the surface of revolution 88 and 90 will be centered on the axis 62-RA and, as shown in FIG. 2, would come to a focus or point of confluence 94. This is approximately the same distance from the center of the ring 62 as the point 120 along the axis 48.

In FIG. 2, the photodetector 96 is arranged so that its sensitive surface is located right at the point 94. In FIG. 4, which is a modified form of the invention, instead of focussing on the front face of a photodetector, the ring 62 is focusses on an aperture 126 formed in a suitable diaphragm or iris 128 and the photodetector 96 is spaced beyond the aperture 126. This prevents any radiant energy from reaching the photocell 96 except that from the mirror ring or segment 62. The small central mask 130 is included to block any rays proceeding from stay reflections inside the inner diameter of ring 124.

All of the rings or segments of the mirror 44 would be so treated as shown for the single ring 62 in FIG. 4.

Figure 5:
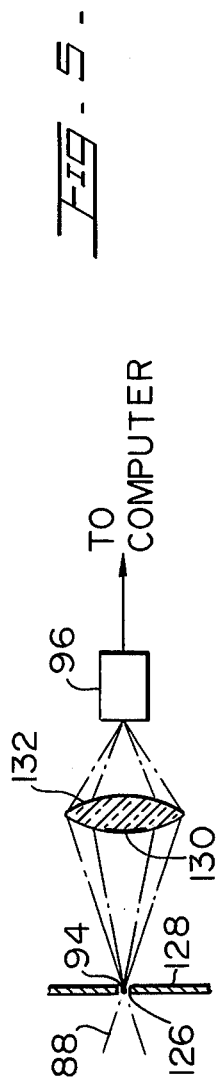

In FIG. 5 only a fragment of the cone of radiant energy is shown at 88 focussed on the aperture 126 of an iris 128. Instead of placing the photocell 96 in position to receive the light directly from the aperture 126, a lens 132 is interposed, the emergent light being focussed on the face of the photocell. Thus, very small efficient photocells may be used. The mask 130 is now applied as opaque paint to the lens faces. As assembly of such lenses for all of the photocells could be molded of economical synthetic resin with areas that are not required for light transmission blocked off with opaque coating material.

Figure 6:
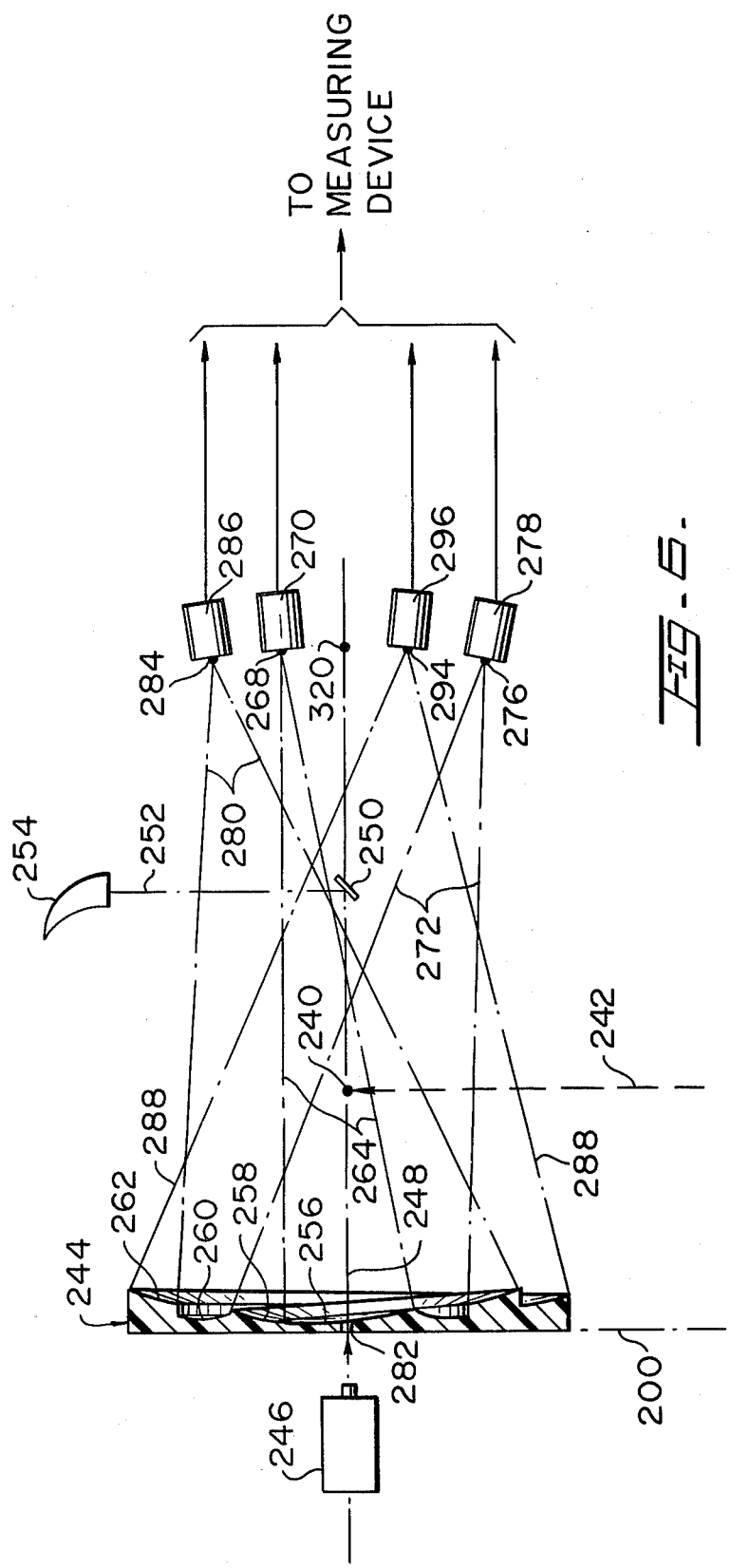
FIG. 6 is a view similar to that of FIG. 2 but of a form of the invention applied to apparatus for measuring back scattering instead of forward scattering.

In FIG. 6 there is illustrated a view similar to that of FIG. 2 but in this case the apparatus is intended for measuring back scattered radiant energy. Additionally, the collecting and deviating device 244 is shown embodying the technique mentioned above for making a practical device. The composite mirror 244 has been molded from an integral member of synthetic resin, for example, and is quite thin and economical to make.

The composite mirror 244 of FIG. 6 has four annular segments or rings 256, 258 260 and 262 which are formed on the front surface, the mirror being otherwise an integral member of plastic or the like. Each of these rings has a silvered coating to render the same reflective. The rear surface of the mirror 244 is flat and lies in the plane 200. Again in this embodiment, all of the surfaces 256, 258, 260 and 262 have been derived from a common spherical mirror surface and the number of rings is small for simplification of the view and the explanation, but this is not essential. The radius of curvature of the principal spherical mirror surface has been increased so that the resulting composite mirror need not be as thick as in the case of the mirror 44 of FIG. 2, but of course this is a matter of the space and requirements of the apparatus. Increasing the radius of curvature will extend the points of confluence of the ring surfaces 256, 258, 260 and 262 beyond the distance of those equivalent of FIG. 2.

The sensing zone or scatter point is shown at 240, being the intersection of a stream of particles 242 with the axis 248. Since this apparatus is intended primarily for the measurement of back scattering, there is a small aperture 282 in the center of the mirror 244 which is also centered in the spherically concave surface 256 and there is a beam of radiant energy directed through this aperture from the left hand side or rear of the mirror 244. This beam is coincident with the optical or central axis of the mirror 244 and originates for example in a low powered laser 246. The beam of light is a fine pencil and intersects the particle stream 242 at the scatter point 240. Any light or radiant energy which continues along the axis 248 to the right of the scatter point or sensing zone 240, as for example during periods when there is no particle in the stream 242, will be collected by the small angled mirror 250 and reflected laterally along the line 252 to the light dump 254. The light dump may also be mounted directly on the optical axis between and behind the array of photocells 278–286.

Light striking particles will be scattered backward toward the mirror 244 and be captured or collected by the ring surfaces 256,258,260 and 262, each ring being effective to collect only a specific geometric area of radiant energy of the back scattered light. As in the case of the apparatus of FIG. 2, the several rings are tilted slightly up and down with respect to the axis 248, but in this view none of the optical or reflective axes of these rings is shown. The tilted angles are chosen to be approximately the same as the angles of FIG. 2 for the rings having the same reference numerals but without the prefix "2". The cones of radiant energy for the rings 256, 258, 260 and 262 are illustrated in FIG. 6 and these comprise the solid cone defined by the outer surface 264, the hollow cone defined by the outer surface 272, the hollow cone defined by the outer surface 280 and the hollow cone defined by the outer surface 288. The inner surfaces of the respective hollow cones are not shown but can readily be provided in the drawing by extending lines from the inner boundaries of the respective rings to the points of confluence of the radiant energy deviated by them.

The points of confluence of the respective rings are at 268, 276, 284 and 294 for the respective rings 256, 258, 260 and 262. These are located generally about the same distance from the center of the mirror 244 as the point of focus 320 on the axis 248 would be if the mirror 244 were a complete unbroken surface spherical mirror whose radius of curvature was the same all over its said surface. The confluence points are laterally spaced from the axis 248 for the same reason as the points of confluence 68, 76, 84 and 94 are spaced from the axis 48. Since the radius of curvature of the mirror 244 is greater than that of the mirror 44 in the illustrations, the distance of the focal point 320 from its mirror 244 is greater than the distance of the focal point 120 from its mirror 44.

There is a photodetector at each of the confluence points of the structure of FIG. 6, these being 270, 278, 286 and 296, all being coupled to some type of measuring device through suitable connections in the same manner as the photodetectors of FIG. 2. The same purifying means may be used in this case as in the case of FIGS. 4 and 5 for each of the cones of radiant energy.

Reference has been made above to the rings 56, 58, 60 and 62 as segments. Likewise the ring surfaces 256, 258, 260 and 262 could be referred to as segments or arcuate elements. It is feasible and practical to use partial rings instead of full rings in forming the composite mirror. Likewise, all of the rings of a given composite mirror need not be derived from the same spherical mirror but could be derived from plural mirrors having different curvatures so that the locations of the points of confluence can be spaced axially relative to axis 48. These points can thus be chosen according to the maximum of convenience for any given apparatus.

The word "confluence" is used herein as a noun according to its normal use and additionally as a verb to signify the tapered directing of a cone of radiant energy toward its apex.

It is not deemed necessary to propose all of the variations in the invention which are capable of being made since those skilled in this art will understand and appreciate that the invention provides a wide latitude in application. The definition of the invention is to be limited only by the appended claims.

What it is desired to secure by Letters Patent of the United States is:

1. Apparatus for measuring the scattering of radiant energy produced by particles for identification or the like of the said particles which comprises:
   A. a source of radiant energy arranged to project a beam of radiant energy along a path,
   B. a sensing zone,
   C. means for moving particles through said sensing zone on an angle relative to said path to produce scattering of radiant energy from said beam,
   D. combined collecting and deviating means for receiving some of the scattered radiant energy and reflecting the same selectively with respect to different geometric portions of the scattered energy to confluence points at locations laterally spaced from said first axis, said collecting and deviating means comprising
      i. an assembly of spherical mirror elements having their reflective surfaces facing the sensing zone, said assembly having a central first axis passing through said sensing zone,
      ii. each element being of a configuration and location to receive and collect radiant energy from a different geometric portion,
      iii. each element having an optical second axis, said element being oriented with respect to the first axis such that its own optical second axis diverges from the said first axis such that it deviates the radiant energy it collects by reflection along a third reflective axis which is twice the angle between the first and second axes to a point of confluence of the deviated radiant energy that is spaced laterally from the first axis,
      iv. the confluence point locations being spaced apart from one another in addition to being spaced laterally from the first axis and
   E. means responsive to the intensity of radiant energy at each location.

2. The apparatus as claimed in claim 1 in which the said beam of radiant energy is coincident with said first axis.

3. The apparatus as claimed in claim 2 in which the mirror elements all derive from the same optical dimensions spherical mirror.

4. The apparatus as claimed in claim 2 in which the mirror elements are all annular.

5. The apparatus as claimed in claim 2 in which the sensing zone is located between the collecting and deviating means and the source of radiant energy whereby to enable the collecting of forward scattered radiant energy.

6. The apparatus as claimed in claim 1 in which the collecting and deviating means and the source of radiant energy are both on the same side of said sensing zone.

7. The apparatus as claimed in claim 2 in which the collecting and deviating means and the source of radiant energy are both on the same side of said sensing zone, the said assembly having a central aperture and being located between the source and sensing zone whereby to enable the collecting of back scattered radiant energy.

8. The apparatus as claimed in claim 1 in which the assembly is an integral article and the elements comprise surface formations on the face of the article.

9. The apparatus as claimed in claim 2 in which the assembly is an integral article and the elements comprise surface formations on the face of the article.

10. The apparatus as claimed in claim 1 in which the means responsive to the intensity of radiant energy comprise a plurality of independent photodetectors, one being located at least adjacent to if not at each confluence point location.

11. The apparatus as claimed in claim 2 in which the means responsive to the intensity of radiant energy comprise a plurality of independent photodetectors, one being located at least adjacent to if not at each confluence point location.

12. The apparatus as claimed in claim 10 in which there is an iris having an aperture interposed between each photodetector and its arcuate element and the confluence point individual to that element is at the aperture rather than at the photodetector.

13. The apparatus as claimed in claim 11 in which there is an iris having an aperture interposed between each photodetector and its associated element and the confluence point individual to that element is at the aperture rather than at the photodetector.

14. The apparatus as claimed in claim 12 in which means are provided to block radiant energy from direct impingement on the geometric center of each photodetector.

15. The apparatus as claimed in claim 13 in which means are provided to block radiant energy from direct impingement on the geometric center of each photodetector.

16. The apparatus as claimed in claim 12 which includes optical means between each aperture and its associated photodetector for additionally focussing the radiant energy onto its said photodetector.

17. The Apparatus as claimed in claim 13 which includes optical means between each aperture and its associated photodetector for additionally focussing the radiant energy onto its said photodetector.

18. A composite mirror of multiple reflecting surface elements adapted to receive distributed radiant energy from a source that is directing such radiant energy in a conical solid angle generally along a principal optical axis directed toward the composite mirror, said mirror adapted to reflect at least portions and at most all of the radiant energy it receives back towards said source generally but along reflective axes which diverge from said principal optical axis so that different surface elements will receive different geometric zones of the distributed radiant energy and reflect and cause confluence of the energy in the respective zones at different locations laterally of the principal optical axis where the energy can be measured, said surface elements each being derived from and comprising a portion of a spherical mirror whose individual optical axis is tilted by a first angle relative to said principal optical axis whereby its reflective axis diverges from said principal optical axis at an angle which is twice said first angle.

19. The composite mirror as claimed in claim 18 in which the surface elements are joined in a single integral structure.

20. The composite mirror as claimed in claim 18 in which all of the surface elements are all derived from the same curvature spherical mirror.

21. The composite mirror as claimed in claim 18 in which the elements are all annular and of different diameters.

22. The composite mirror as claimed in claim 18 in which at least some of the elements have different first angles of tilt.

23. The composite mirror as claimed in claim 18 in which all of the elements have first angles of tilt differing from one another whereby all of the points of confluence are spaced differently from the principal optical axis.

24. The composite mirror as claimed in claim 21 in which the center element is circular and has a central aperture for passage of a radiant energy beam to the source.

25. A method of measuring the directional distribution properties of a particle for particle identification or the like which comprises:
  A. passing the particle through a sensing zone and illuminating the particle with an incident beam of radiant energy whereby to produce reactive directional distribution of the radiant energy as a result of the intersection of particle and beam,
  B. intercepting a portion of the radiant energy which is directionally distributed and which is projected to the location of interception in a conical solid angle whose approximate principal optical axis extends between the point of intersection and the location of interception,
  C. reflecting the intercepted radiant energy along a plurality of different paths which diverge from the principal axis and confluence at locations laterally of the axis,
    i. each path being arranged to comprise the radiant energy intercepted from an arcuate solid angle of the projected portion,
    ii. the arcuate areas being different from one another,
    iii. the axis of each path being a reflective axis
    iv. the locations of confluence being spaced from one another, and
  D. measuring the respective intensities of the radiant energy at the locations of confluence.

26. The method as claimed in claim 25 in which the properties measured are the scattering properties of the particle and the intersection of the particle and beam causes scattering.

27. The method as claimed in claim 26 in which the arcuate solid angles of the projected portion comprise cones of radiant energy and each path is individual to a different cone, the cones being of increasing size from the center principal axis radially outward and encompassing substantially all of the intercepted radiant energy, the number of paths being equal to the number of cones.

28. The method as claimed in claim 26 in which the particle is illuminated from a source which is also directed toward the location of interception whereby the radiant energy measured comprises forward scattered radiant energy.

29. The method as claimed in claim 26 in which the particle is illuminated from a source that is directed through the location of interception whereby the radiant energy measured comprises back scattered radiant energy.

30. The method as claimed in claim 27 wherein the reflecting is effected in the manner of reflection from spherical mirror elements.

* * * * *